(12) United States Patent
Mikus et al.

(10) Patent No.: US 10,470,789 B2
(45) Date of Patent: Nov. 12, 2019

(54) METHOD FOR REDUCING OR REMOVING BIOFILM

(71) Applicant: MISONIX, INCORPORATED, Farmingdale, NY (US)

(72) Inventors: Paul Mikus, Trabuco Canyon, CA (US); Dan Voic, Cedar Grove, CA (US); Scott Isola, Deer Park, NY (US)

(73) Assignee: MISONIX, INC., Farmingdale, NY (US)

( * ) Notice: Subject to any disclaimer, the term of this patent is extended or adjusted under 35 U.S.C. 154(b) by 126 days.

(21) Appl. No.: 15/450,818

(22) Filed: Mar. 6, 2017

(65) Prior Publication Data

US 2018/0250031 A1 Sep. 6, 2018

(51) Int. Cl.
| | | |
|---|---|---|
| *A61B 17/20* | (2006.01) | |
| *A61B 17/32* | (2006.01) | |
| *A61M 1/00* | (2006.01) | |
| A61B 17/00 | (2006.01) | |
| A61L 2/00 | (2006.01) | |

(52) U.S. Cl.
CPC ... *A61B 17/320068* (2013.01); *A61M 1/0035* (2014.02); *A61M 1/0086* (2014.02); *A61B 2017/00402* (2013.01); *A61B 2017/00477* (2013.01); *A61B 2017/00747* (2013.01); *A61B 2017/00761* (2013.01); *A61B 2017/32007* (2017.08); *A61B 2017/320012* (2013.01); *A61B 2017/320072* (2013.01); *A61B 2017/320073* (2017.08); *A61B 2017/320078* (2017.08); *A61B 2017/320084* (2013.01); *A61B 2217/005* (2013.01); *A61L 2/0005* (2013.01)

(58) Field of Classification Search
CPC .. A61B 17/320068; A61B 2017/00402; A61B 2017/320084; A61B 2017/00477; A61M 1/0035; A61M 1/0086; A61M 2205/058; A61M 1/0084
See application file for complete search history.

(56) References Cited

U.S. PATENT DOCUMENTS

| | | | |
|---|---|---|---|
| 7,494,488 | B2 | 2/2009 | Weber |
| 7,905,848 | B2 | 3/2011 | Cuypers et al. |
| 2010/0049188 | A1 | 2/2010 | Nelson et al. |
| 2016/0128707 | A1 | 5/2016 | Mikus et al. |
| 2016/0128708 | A1* | 5/2016 | Mikus ............ A61B 17/22004 606/110 |

* cited by examiner

*Primary Examiner* — Rebecca E Eisenberg
(74) *Attorney, Agent, or Firm* — R. Neil Sudol; Henry D. Coleman

(57) ABSTRACT

A method for reducing or removing biofilm on a target tissue or prosthesis surface includes providing a coupling space or antechamber between the operative tip or end of an ultrasonic probe and a target treatment surface, the space or antechamber being fillable with a liquid irrigant to transmit ultrasonic vibration and facilitate extraction of biofilm fragments including potentially pathogenic particles. A second phase of treatment in the case of organic tissue involves the attachment of one or more ultrasonic transducers to a patient over or near a surgical treatment site after surgery is terminated. Each applied ultrasonic transducer is used to vibrate the patient's tissues at the treatment site to disrupt biofilm formation.

16 Claims, 10 Drawing Sheets

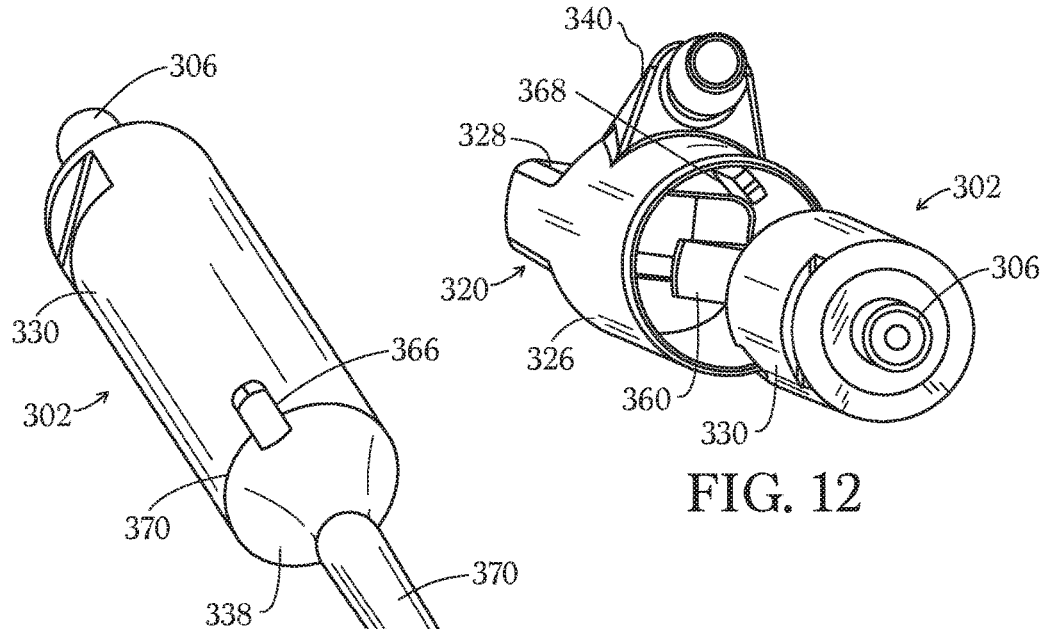
FIG. 11
FIG. 12
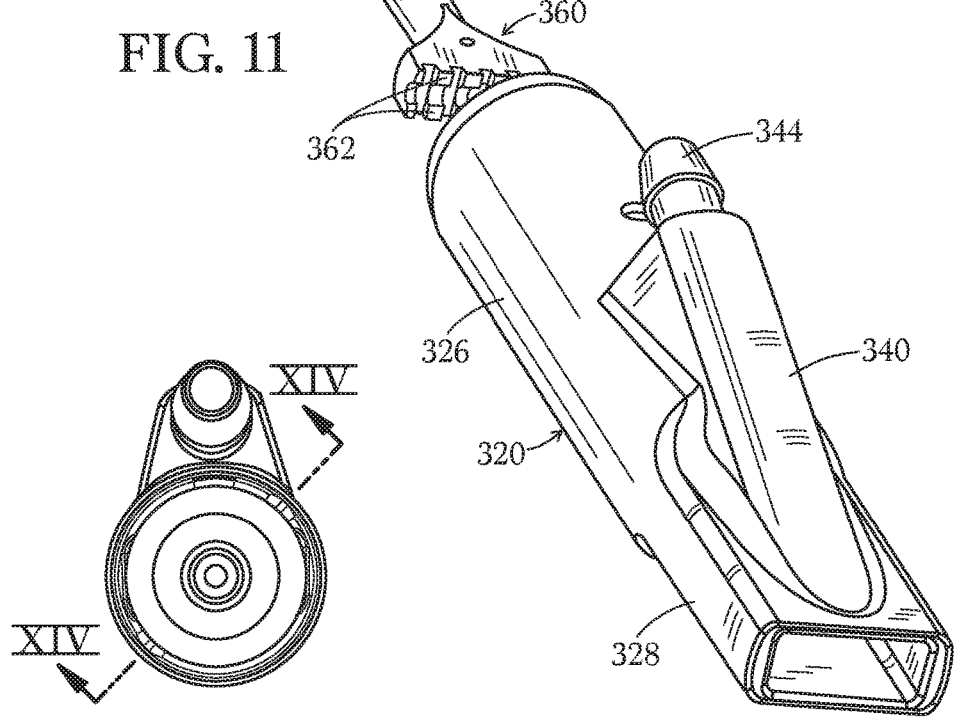
FIG. 13

METHOD FOR REDUCING OR REMOVING BIOFILM

BACKGROUND OF THE INVENTION

This invention relates to apparatus and method for reducing or removing biofilm. The target biofilm may be on a wound site particularly a wound site that is being debrided to remove necrotic tissue. Alternatively, the target biofilm may be on a prosthetic device or component that is either in situ in a patient, or removed from the patient for cleaning and re-implantation.

Chronic wound infection represents a significant healthcare problem worldwide. Often the end objective of wound healing is the objective for new therapeutic options. Yet chronic wounds compromise a number of different and complex conditions that each interferes with the healing process. For example, a chronic wound can comprise necrotic tissue in need of debridement, bacterial infection in need of antimicrobial agents and compromised vasculature that impedes the normal healing process.

One element of the chronic wound infection condition that impedes healing is the formation of biofilm. Biofilm is the result of planktonic bacteria forming together and secreting exopolysaccharide (EPS) to adhere and protect the colonizing community. At the height of formation, EPS can make up between 75-90% of the total biofilm composition (Regt). Biofilm inhibits healing by creating an optimal condition for bacteria to grow, while simultaneously preventing antimicrobial agents from direct access to bacteria.

Methods to remove biofilm include ultrasonic debridement, topical antimicrobials, suction, and surface cleansing. Each of these methods alone treat an aspect of biofilm. For example, ultrasonic debridement of wounds has proven to be the most effective mechanism in disrupting and debulking a majority of the biofilm formation. Yet even in this preferred method, biofilm debris can be left behind to propagate. Suction alone has not proven to be effective in removing biofilm, and can potentially interfere with the operation of other methods like ultrasonic debridement if applied simultaneously.

U.S. Pat. No. 7,608,054 to Soring et al. describes a medical treatment apparatus that combines an ultrasound sonotrode with a suction sheath. The fixed position between the tip of the suction and the tip of the sonotrode only allows for one simultaneous operation. In particular this approach is limited due to the potential interference of the suction tip during the ultrasonic debridement operation.

U.S. Pat. No. 7,522,955 B2 to Rontal et al. describes a method and apparatus for ultrasonic cleaning of biofilm coated surfaces for sinus cavities within a human head. The method describes an ultrasonic application in combination with irrigation and suction that is designed to not remove any of the surrounding underlying tissue. This differs significantly from an ultrasonic debridement of a wound bed, which requires the removal of tissue in combination with biofilm. Thus the ultrasonic probe needs to operate in a cavitation mode at the surface of a wound, causing destruction of the biofilm.

Methods of mechanical removal of biofilm in wounds alone have proven to be inadequate. What does not exist and what would be beneficial to the market is a method to remove biofilm and prevent it from reforming in order to allow wounds to heal.

A particular kind of wound in which biofilm may form is at a site of prosthesis implantation. It is not uncommon for infection to crop up at sites of prosthetic implants. Frequently the prostheses must be removed in whole or in part to enable cleaning of the implantation site. In addition, the prosthetic parts, which are generally reinserted into the patient must be cleaned of biofilm.

OBJECTS OF THE INVENTION

It is an object of the present invention to provide a method to inhibit or reduce biofilm formation in or on wounds in order to allow wounds to heal more expeditiously.

A related object of the present invention is to provide a method for removing biofilm from wound sites so as to reduce the likelihood of the biofilm reforming.

The present invention is also directed to a method of removing biofilm, not only from wound sites but also from prostheses or prosthetic parts.

A more particular object of the present invention is to provide such a method for removing biofilm which reduces and preferably minimizes any dispersion of atomized fluid particles from the target treatment site, including wound sites but also including surfaces of prostheses which have been removed from a host or patient.

It is an associated object of the present invention to provide apparatus for removing biofilm with structure to assist not only in biofilm reformation reduction but also in reduction of particle dispersion during the treatment or cleaning process.

Although every feature of the invention is attained in at least one embodiment of the invention, there is not necessarily any one embodiment that achieves all of the objects of the invention.

SUMMARY OF THE INVENTION

The present invention broadly contemplates a method for the inhibition of biofilm on wounds and injured organic tissues, and concomitantly a method for reducing the likelihood of biofilm formation on treated tissues. The method additionally contemplates a surgical room cleansing process and a disruption and removal of biofilm from hard surfaces and exemplarily from surgical instruments and prosthesis components.

A medical therapeutic method in accordance with the present invention utilizes an ultrasonic debridement instrument having a probe with an operative tip and a first channel. The instrument includes a sheath or sleeve with a distal tip, the sheath or sleeve defining a second channel extending outside the probe. The second channel has an inlet proximate the distal tip of the sheath or sleeve. The method comprises manipulating the instrument to place the distal tip of the sheath or sleeve against a target surface such as a wound site or a surface or a prosthesis needing cleaning. The instrument is manipulated to place the sheath or sleeve so that it extends in part distally of the operative tip of the probe and serves in part to maintain or create a spacing between the probe's operative tip and the target surface. The manipulating of the instrument to place the distal tip of the sheath or sleeve against the target surface inherently positions the operative tip at a distance from the target surface. This distance defines a space, chamber or fluid-holding area that constitutes an ultrasound coupling zone wherein irrigation liquid is temporarily contained. The irrigation fluid thus captured between the operative tip of the probe and the target surface serves to (a) transmit ultrasonic pressure waves to the target surface from the operative probe tip, (b) capture, entrain and emulsify biofilm fragments generated by the ultrasonic pressure waves or cavitation at the target surface, and (c)

facilitate removal of the biofilm fragments as well as any toxins such as bacteria that may be present in the biofilm.

During contact of the distal tip of the sheath or sleeve with the target surface, one feeds an irrigation fluid through the channel in the probe to a region between the operative tip of the probe and the target surface. Also during contact of the distal tip of the sheath or sleeve with the target surface, an ultrasonic standing wave is generated in the probe to vibrate the operative tip thereof and thereby fragment undesired material at or on the target surface. During the generating of the ultrasonic standing wave, vacuum or negative pressure is applied to the second channel to remove fluid from the target surface.

Pursuant to another feature of the present invention, the sheath is slidably mounted so that the sheath or sleeve is longitudinally shiftable relative to the probe. The method then further comprises shifting the sheath or sleeve in a distal direction along the instrument prior to the manipulating of the instrument to place the distal tip of the sheath against the target surface. Variability in the longitudinal position of the sheath or sleeve relative to the probe enables the user to adjust the height of the coupling space or chamber between the operative surface of the probe and the target surface. The height may be close to zero, in which case the operative tip of the probe may be placed in contact or near contact with a target surface such as organic tissue at a site of a patient wound or injury.

Typically the second channel is located between the sheath or sleeve and the probe of the instrument. The method may also comprise shifting the sheath or sleeve in a proximal direction after the generating of the ultrasonic standing wave and thereafter applying a vacuum or negative pressure to the second channel to suck ambient air into and through the second channel.

Preferably, the irrigation fluid includes a disinfectant or biocide such as hypochlorous acid and/or metal ion hypochlorite. This disinfectant or biocide is advantageously generated on site, at or immediately prior to the treatment by ultrasound, thereby ensuring an effective concentration of the hypochlorous acid. The hypochlorous acid and/or metal ion hypochlorite may be produced from a sterile saline solution through an electrolytic process.

A surgical device in accordance with the present invention comprises an ultrasonic probe having an operative tip and a first channel extending longitudinally therein. An electromechanical transducer is operatively connected to the probe for generating an ultrasonic standing wave in the probe to vibrate the operative tip at ultrasonic frequency. At least one sheath or sleeve is disposed about the probe and defines a second channel outside the probe. The second channel has at least a first port in a region about a distal end of the probe, proximate the operative tip. The sheath or sleeve has an operative configuration wherein a distal end portion of the sheath or sleeve extends distally beyond the operative tip of the probe to define or enclose an ultrasound coupling space between the operative tip and a target surface.

During the use of the instrument, an irrigant is delivered to the distal end of the probe preferably through the first channel but possibly through the second channel and accumulates to act as a coupling medium in the space between the operative tip of the probe and a selected target surface. The ultrasonic vibrations are transmitted through the coupling medium irrigant from the probe tip to generate disruptive cavitation or other micron-sized mechanical and thermal disturbances at the target surface.

The distal end portion of the sheath or sleeve, the operative tip of the probe, and the target surface define a chamber or enclosure that (1) ensures a separation of the operative probe tip from the target surface and yet (2) enables effective coupling for ultrasound pressure wave transmission, owing to the containment of liquid irrigant in the chamber or enclosure, while reducing spray or atomized detritus and containing the detritus and potential pathogenic particles for removal via the suction channel in the sheath or sleeve.

Pursuant to another feature of the present invention, the sheath or sleeve is longitudinally slidable relative to the probe to shift between a distal or extended position in the operative configuration and a proximal or retracted position. In the distal-most or extended position of the sheath or sleeve the probe head is covered while in a proximal-most position of the sheath or sleeve at least a portion of the probe head is exposed. The instrument may be provided with a locking mechanism, such as a set screw, a clamp, or a friction fit, which holds the sheath or sleeve in either the extended position or the retracted position, and optionally any position therebetween.

Preferably, the probe and the sheath or sleeve define a first space or channel and a second space or channel generally laterally or to the side of the probe, the second space or channel being located proximally of the first space or channel and having a larger transverse cross-sectional area, in a plane orthogonal to an axis of the probe, than the first space or channel. The probe may be provided at or in a distal end portion with at least one aperture spaced from the outlet and communicating with the first space or channel, the sheath being provided with an aspiration arm having an aspiration channel communicating with the first space or channel and the second space or channel.

The probe may exemplarily include a proximal body section, a smaller-diameter horn section, and a probe head. The horn section extends distally of the body section, and the head is formed at a distal end of the horn section.

In a specific embodiment of the present invention, the distal end portion of the sheath or sleeve is formed with a plurality of longitudinally extending fingers separated by one or more gaps or spaces. In another specific embodiment of the present invention, the distal end portion of the sheath or sleeve is formed with one ore more one apertures in a sidewall, the aperture(s) being spaced from the distal edge or tip of the sheath or sleeve. The gaps and apertures serve as air inlets for the ingress of air into the coupling space or chamber, which enables the removal of the coupling medium and collected detritus via a suction port typically at the proximal end of the coupling space or chamber, and which serves to prevent the egress of atomized irrigant and pathogenic particles from the treatment zone. The rate of irrigant flow is preferably sufficiently great not only to remove the biofilm particles and pathogenic components from the treatment site but also to cool the probe and the treatment site, at least in the case of debridement of a wound bed or tissue injury site.

In the treatment or organic tissues, the method typically includes a mechanical (e.g., ultrasound) debridement for the removal of any existing necrotic tissue, surface infection or previously formed biofilm. The mechanical debridement process results in a clean wound bed of healthy granulated tissue. Substantially immediately following the mechanical debridement of a wound, an ultrasound biofilm disrupter pad may be placed on or near the wound to prevent bacterial adherence to the wound bed by excretion of EPS.

The ultrasound biofilm disrupter prevents adherence of bacteria to the wound by application of surface acoustic waves at a sufficient frequency and amplitude to disrupt formation but below a threshold that stimulates bacterial growth. In order to accomplish this, a wound-dressing device, which incorporates a disposable ultrasonic transducer, may be applied to the wound site post debridement for duration sufficient to allow healing to occur.

Ultrasonic debridement, which mechanically removes necrotic tissue while cleansing the wound bed, should be in a frequency range about 20 kHz, e.g., preferably 16-100 KHz, more preferably 16 KHz-25 KHz, and most preferably 20-23 KHz, in order to simultaneously begin the process of biofilm disruption. Once the mechanical debridement is complete, a lower energy setting on the debridement probe may be utilized to pre-condition the wound bed for disrupting adherence or starting the formation of biofilm. Preferably, the wound bed is immediately covered with a wound dressing that incorporates an ultrasonic biofilm disrupter transducer delivering a surface acoustic wave at 20 kHz with an acoustic power output of 0.2-0.4 w/cm$^2$. The transducer is connected to a portable energy source. The energy source can be battery supplied. The wound dressing can incorporate an antimicrobial agent that is delivered during the biofilm disruption treatment.

To discourage biofilm reformation after a debridement operation, an ultrasound transducer or generator may be incorporated into a wound dressing and applied after standard wound cleansing protocols have been administered. These protocols can include saline wash, topical antimicrobial agents applied. The combination of ultrasonic debridement, low-pulsed ultrasonic biofilm disruption and topical antimicrobials produces an important sequential approach to the management and removal of biofilm. The removal of biofilm results in the removal of an impediment to the wound healing process.

Ultrasound is preferably combined with suction as discussed hereinabove to create an optimal combination for disruption and removal of biofilm. One stage of biofilm is an excretion of seeding stage. So existing debridement processes can result in a bulking of the biofilm, but at the same time a seeding of the newly created wound bed. The seeding process can occur from a mechanical debridement alone. In this the process for biofilm disruption is temporary at best. To correct this problem, ultrasonic debridement is combined with a suction process that collects the mechanically removed biofilm remnants or seeding agents. As discussed above, the present method and apparatus provides a cavitation antechamber, as it were, distal of the ultrasonic probe which serves in part to optimize the capture and removal of mechanically removed biofilm remnants or seeding agents.

In this combined ultrasound and suction approach, the ultrasonic debridement probe is housed by a suction probe that optionally operates in two stages. The first stage is with the ultrasonic debridement probe in contact or near contact (via the coupling space or antechamber) with the target tissue and the suction tip surrounding the debridement tip so that it is in contact with the tissue simultaneously to remove the mechanically disrupted biofilm. In the second stage of operation the suction tip can be moved to a position that is not in contact or near contact with the tissue, but sufficient enough to capture any biofilm debris that is propelled into the area.

As indicated above, the combination of ultrasound and suction may have one or more stages of operation. The positioning of the suction tip in relationship to the ultrasound tip can be configured for a variety of different combinations to cause better mechanical disruption and capture of that disrupted biofilm. The combination of both ultrasonic energy to cause debridement and suction to cause removal can be done in a variety of different sequences. For example, ultrasonic mechanical debridement can be performed on the majority of the wound bed prior to engaging suction to capture any remnant amounts of biofilm on the wound bed. In a preferred embodiment the ultrasonic mechanical debridement is performed simultaneous to applying suction either at the tip or near the tip.

The present invention contemplates that the suction is incorporated into the ultrasonic debridement instrument to allow for a mechanical disruption and immediate capture of biofilm fragments. Preferably the suction port is proximate the tip of the ultrasonic debridement probe to allow for maximum capture of the mechanically disrupted biofilm. The sheath or sleeve is disposable (to avoid risk of cross contamination) and incorporates a suction channel for capturing biofilm during an ultrasonic debridement. In one embodiment the sheath has a multiple position for use during an ultrasonic debridement. The sheath can capture both the debris that is expelled during the debridement and any remaining debris at the surface of the wound bed. The sheath may incorporate a sealing strategy to maintain suction pressure while still allowing for multi positioning on the suction tip in relationship to the ultrasonic debridement tip.

In another embodiment, the suction is interspersed throughout the ultrasonic debridement probe so that any area of mechanical disruption has a corresponding area of capture capability.

Accordingly, a medical therapeutic method pursuant to one aspect of the present invention utilizes an ultrasonic debridement instrument having an operative tip and a suction channel. The method comprises (i) manipulating the instrument to place the operative tip against a patient's tissues at a preselected surgical site, (ii) during contact of the operative tip with the patient's tissues, generating an ultrasonic standing wave in the instrument, thereby fragmenting necrotic tissue and undesired organic material at the surgical site, (iii) during the generating of the ultrasonic standing wave, disposing a suction inlet at a distal end of the suction channel proximate the surgical site and (iv) applying vacuum or negative pressure to the suction channel to remove tissue debris fragmented organic material from the surgical site via the suction inlet.

Optionally, in a variation of a debridement or biofilm removal procedure as described herein, one may dispose a suction port at a selected position spaced from the surgical site, and during and/or after the generating of the ultrasonic standing wave and the fragmenting of tissue and material, draw ambient air from a region about the surgical site through the suction port at the selected position. Preferably, the suction port is provided on the ultrasonic debridement instrument, and the method includes operating an actuator to enable the sucking of air through the suction port.

As indicated above, the actuator may include a sheath or sleeve which is slidably mounted to the instrument for longitudinal motion alternately in opposing directions along the shaft or probe portion thereof. The operating of the actuator then includes shifting the sheath or sleeve in an axial direction along the instrument. Where the instrument includes a longitudinally shiftable sheath or sleeve, with the suction channel being located between the sheath or sleeve and a shaft or horn of the instrument, the suction inlet and the suction port may both be defined by the distal end of the sheath or sleeve, the position of the sleeve determining whether an intake opening is located at the operative tip of the instrument, and is thus the suction inlet, or is spaced from the operative tip and is therefore the suction port. Accordingly, the method may further comprise shifting the sheath or sleeve in a proximal direction after the applying of a vacuum or negative pressure and prior to the sucking of the ambient air through the suction port, a distal tip of the sheath or sleeve defining the suction inlet in a distal position of the sheath or sleeve, the distal tip defining the suction port in a proximal position of the sheath or sleeve.

In the variation of a debridement or biofilm removal procedure, it is contemplated that the suction inlet and the suction port may be different and always mutually spaced from one another. If the instrument includes a slidable sheath or sleeve, the position of that element may determine whether the suction inlet and/or the suction port is active. Thus, the sheath or sleeve may include valves for opening and closing air pathways extending to the suction inlet and the suction port, in dependence on the longitudinal position of the sheath or sleeve. Alternatively, valves may be operated separately via respective electromechanical actuators so that the opening and closing of the suction inlet is controllable independently of the opening and closing of the suction port.

Thus, where the suction port is different from the suction inlet, the suction port being located proximally along the instrument from the suction input, the operating of the actuator may include directing suction under-pressure to the suction port. The actuation may include operating a valve to open a suction pathway to the suction port.

Where the invention is used in a surgical procedure on tissues of a patient, the method may alternatively or additionally comprise placing an ultrasonic transducer on the patient at least proximate the surgical site after terminating of a debridement process and while the surgical site is free of discernible bacteria. Typically, the transducer is placed immediately after the surgical site has been cleaned of necrotic tissue and other undesirable debris and even prior to the removal of the patient from the operating room. After the placing of the transducer and while the transducer is in effective vibration-transmitting contact with the patient, an electrical energization waveform of an ultrasonic frequency is conducted to the transducer at least intermittently during a period of approximately one day or longer to prevent biofilm formation on the patient at the surgical site and facilitate a healing of the patient's tissue at the surgical site.

The transducer may be affixed to a carrier pad, the placing of the transducer on the patient including attaching the pad to the patient. Alternatively, the transducer may be disposed in a balloon or bladder inflated with a gel or other medium conducive to the effective transmission of ultrasonic pressure waves, the balloon or bladder being attached to the patient over or adjacent the surgical site. Other transducer carriers and methods of attachment to the patient will occur to those skilled in the art.

Accordingly, a medical therapeutic method comprises (a) removing necrotic tissue and undesired organic material from a surgical site on a patient, (b) shortly thereafter, while the surgical site is free of discernible bacteria, placing at least one ultrasonic transducer on the patient at least proximate the surgical site, and (c) after the placing of the transducer and while the transducer is in effective vibration-transmitting contact with the patient, conducting an electrical energization waveform of an ultrasonic frequency to the transducer at least intermittently during a period of approximately one day or longer, the waveform having frequency, amplitude and duration to effectively reduce formation on the patient at the surgical site and thereby facilitate a healing of the patient's tissue at the surgical site. The placing of the transducer preferably includes removably attaching the transducer to the patient atop tissues at the surgical site.

A surgical device described below comprises an ultrasonic probe having an operative tip, an electromechanical transducer operatively connected to the probe for generating an ultrasonic standing wave in the probe, and at least one sheath or sleeve disposed about the probe and defining at least a first suction port at a distal end of the probe, proximate the operative tip, and a second suction port spaced from the distal end of the probe.

The one or more sheaths or sleeves may take the form of exactly one sheath or sleeve slidably attached to the probe to shift between a distal position and a proximal position, wherein a distal end of the sheath or sleeve is alternately locatable (i) proximate the operative tip to define the first suction port and (ii) at a predetermined distance from the operative tip to define the second suction port.

Alternatively, the first suction port and the second suction port are different openings in the at least one sheath or sleeve. Their operational status may be separately controlled via respective valves. Moreover, the suction ports may be connectable to vacuum sources of different strengths. The magnitude of the vacuum or negative pressure applied to the proximal port is typically greater than the magnitude of the vacuum or negative pressure applied to the distal port.

The sheath or sleeve may define a first suction channel extending to the first suction port and a separate second suction channel extending to the second suction port, the first suction channel and the second suction channel being subjectable to different negative pressures.

Described herein is a method for bacterial containment during application of therapeutic ultrasound application. In a preferred embodiment, a suction device is incorporated adjacent to the therapeutic ultrasound applicator to create a path of removal for any bacteria that is being displaced during the treatment. The suction device is incorporated in such a way as to orient the orifice of the suction to favorably capture any projected, predicted or anticipated paths of spray the would result from the applicator tip interacting with the targeted treatment site. In this the suction device is optimized for the preferential capture of any bacteria that is displaced by the tissue removal during debridement. The suction device can also be used to contain irrigation spray that results from the application of therapeutic ultrasonic energy.

In another embodiment the suction device is integrated into the treatment probe so that is has ports of capture that are strategically placed to remove bacteria that is displaced during tissue removal during debridement. The suction device is incorporated in such a way as to orient the orifice of the suction to favorably capture any projected, predicted or anticipated paths of spray the would result from the applicator tip interacting with the targeted treatment site. The suction device can also be used to contain irrigation spray that results from the application of therapeutic ultrasonic energy.

In another embodiment the suction device is separate from the treatment probe but is used in coordination to capture any bacteria that is displaced by the tissue removal during debridement. The suction device can be strategically placed adjacent to the treatment area in such a manner that the opening of the suction device creates a preferential path for the capture of displaced bacteria. The suction device can be a ring that defines a specific treatment area around the ultrasound applicator. The ring device has capture ports that are oriented inward towards the potential treatment areas so that in any direction capture of bacteria that is displaced from the treatment site. The suction device is incorporated in such a way as to orient the orifice of the suction to favorably capture any projected, predicted or anticipated paths of spray the would result from the applicator tip interacting with the targeted treatment site. The suction device can also be used to contain irrigation spray that results from the application of therapeutic ultrasonic energy. The suction device can be secured to the patient temporarily so that it creates a barrier for the bacteria or irrigation spray to be able to get beyond. The temporary attachment can be a strap, a skin friendly adhesive pad, or another easy to place easy to remove approach.

In another embodiment, a suction device is incorporated adjacent to the therapeutic ultrasound applicator to create a path of removal for any bacteria that is being displaced during the treatment. The suction device has two or more position of use. In the first position the suction device is incorporated in such a way as to orient the orifice of the suction to favorably capture any projected, predicted or anticipated paths of spray the would result from the applicator tip interacting with the targeted treatment site. In this the suction device is optimized for the preferential capture of any bacteria that is displaced by the tissue removal during debridement. In the second position the suction device is incorporated in such an way to come into direct contact with the targeted treatment surface to allow for direct removal of any residual bacteria. The suction device can also be used to contain irrigation spray that results from the application of therapeutic ultrasonic energy.

In another embodiment suction device is incorporated into a therapeutic ultrasound applicator that delivers an irrigation stream to the applicator tip. The suction device is a disposable sheath incorporated adjacent to the therapeutic ultrasound applicator to create a path of removal for any bacteria or irrigation spray that is being displaced during the treatment. The suction device is incorporated in such a way as to orient the orifice of the suction to favorably capture any projected, predicted or anticipated paths of spray the would result from the applicator tip interacting with the targeted treatment site. In this the suction device is optimized for the preferential capture of any bacteria that is displaced by the tissue removal during debridement. The suction device can also be used to contain irrigation spray that results from the application of therapeutic ultrasonic energy.

In another embodiment suction device is incorporated into a therapeutic ultrasound applicator that delivers an irrigation stream to the applicator tip. The suction device is a disposable sheath that is molded onto the single use ultrasound treatment probe to create a path of removal for any bacteria or irrigation spray that is being displaced during the treatment. The suction device is incorporated in such a way as to orient the orifice of the suction to favorably capture any projected, predicted or anticipated paths of spray the would result from the applicator tip interacting with the targeted treatment site. In this the suction device is optimized for the preferential capture of any bacteria that is displaced by the tissue removal during debridement. The suction device can also be used to contain irrigation spray that results from the application of therapeutic ultrasonic energy.

BRIEF DESCRIPTION OF THE DRAWINGS

FIG. 11 is an exploded right side, top and front perspective view of a probe and sheath included in the device of FIGS. 9 and 10.

FIG. 12 is an exploded left side, top, and rear perspective view of the probe and sheath of FIGS. 9-11.

FIG. 13 is a rear elevational view of the probe and sheath of FIGS. 9-12.

DETAILED DESCRIPTION

Figure 1:
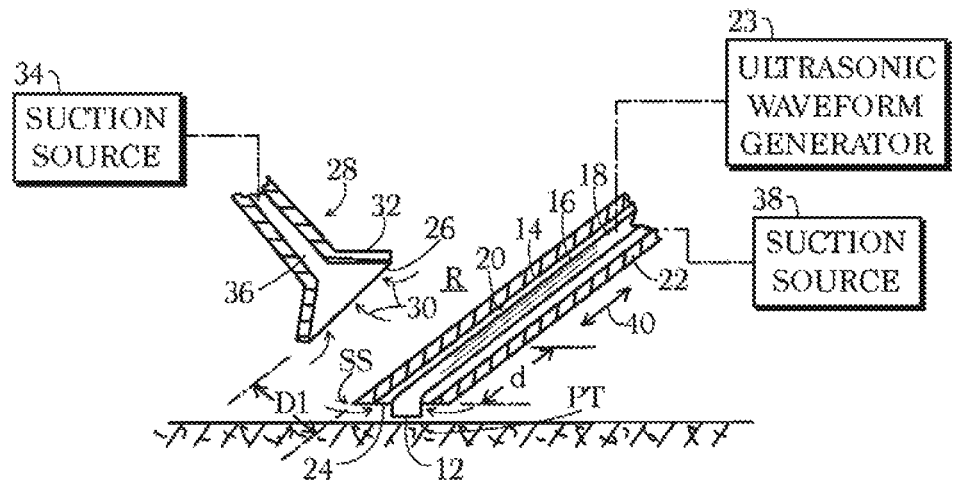
FIG. 1 is partially a schematic cross-sectional view and partially a block diagram of a system for removing biofilm from a wound site and reducing the likelihood of biofilm reformation thereafter.

The present disclosure contemplates a two phase method for reducing the formation of biofilm. The first phase is performed where a wound site is being treated for removal of necrotic tissue, eschar or biofilm and includes an evacuation of ambient air from a region about the surgical or treatment site, to extract airborne or aerosolized bacteria ejected from the site by the treatment. The extracted bacteria are prevented from settling back onto the cleansed tissue surface, thus at least reducing colonial bacteriological growth and concomitantly exuded biofilm material. The second phase or approach for reducing biofilm involves the attachment of one or more ultrasonic transducers to the patient over or near a surgical treatment site after the surgery is terminated. Each applied ultrasonic transducer is used to vibrate the patient's tissues at the treatment site to disrupt biofilm formation. The two phases of treatment may be used separately depending on the application. Thus, ultrasonic biofilm disruption may be used at wound sites which have not been subjected to formal processes for removal of necrotic tissue, eschar or biofilm.

Accordingly, a medical therapeutic method may utilize an ultrasonic debridement instrument 10 (FIG. 1) having an operative tip or surface 12 and a suction channel 14 defined between an outer surface 16 of an ultrasonic horn 18 and an inner surface 20 of a cannula or sheath 22. The method comprises manipulating the instrument 10 to place the operative tip or surface 12 against a patient's tissues PT at a preselected surgical site SS. During contact of the operative tip 12 with the patient's tissues PT, one operates a waveform generator 23 to generate an ultrasonic standing wave in the instrument 10 and particularly in probe or horn 18, to thereby fragment necrotic tissue and undesired organic material at the surgical site SS. During the generating of the ultrasonic standing wave, a suction inlet 24 at a distal end of the suction channel 14 is disposed proximate the surgical site SS and a vacuum or negative pressure is applied to the suction channel 14 to suck tissue debris and fragmented organic material from the surgical site SS via the suction inlet 24. A suction port 26 of another instrument 28 is disposed at a position spaced at a distance D1 from the surgical site SS. During and/or after the generating of the ultrasonic standing wave and the fragmenting of tissue and material by instrument 10, instrument 28 is operated to suck ambient air, as indicated by arrows 30, from a region R about the surgical site SS through suction port 26. While suction inlet 24 is typically located between 1 and 5 mm from the surgical site SS and the tissue surface at the surgical site, suction port 26 is typically located 2-6 cm from the tissue surface at the surgical site SS.

As depicted in FIG. 1, instrument 28 may be formed at a distal end with an enlarged or expanded extension 32, such as a cone, to funnel air 30 into the instrument. A suction source or vacuum generator 34 communicating with a lumen 36 of instrument 28 may exert a greater suction force than that of a suction source or vacuum generator 38 communicating with suction channel 14.

In an alternative approach, instrument 28 is omitted. Instead, cannula or sheath 22 is shiftably mounted to probe or horn 18 for longitudinal motion alternately in opposing directions along the shaft or probe portion thereof, thereby enabling the user to position the suction port, defined in part by the distal edge of the sheath, in two or more alternative locations, a most distal location adjacent the operative tip 18 of the probe or horn 12 and a more proximal location. As indicated by a double headed arrow 40, cannula or sheath 22 is pulled in a proximal direction after an operation removing tissue or other organic matter from surgical site SS so that suction port 26 is located at a distance d from the operative tip or surface 12 of instrument 10. An actuator such as suction source 38, or a switch component thereof, is operated to enable the sucking of air through suction port 26 at the retracted position of cannula or sheath 22. In a simple configuration, suction source 38 may have twp operating states, on and off, the position of sheath 22 determining whether suction is applied at the surgical site SS or at a distance therefrom. In a slightly more complicated configuration, suction source 38 may be provided with three operating states, namely, off, high suction and low suction. The degree of suction may be selectable by the operator or may be automatically controlled in accordance with the longitudinal or axial position of sheath 22 along probe or horn 12. For instance, sheath or sleeve 22 may be provided with valves (not shown) for opening and closing air pathways in dependence on the longitudinal position.

Figure 2:
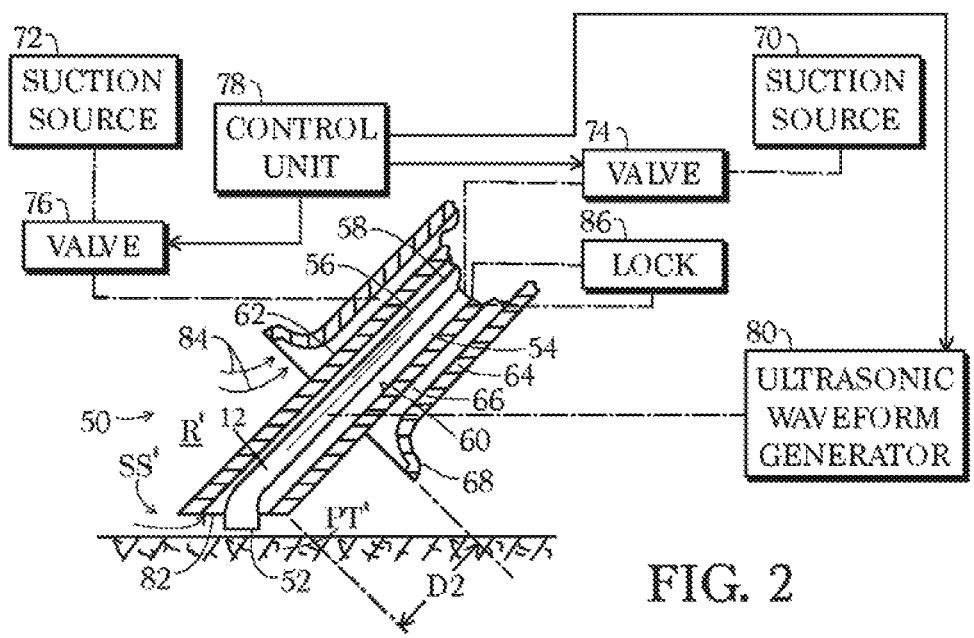
FIG. 2 is partially a schematic cross-sectional view and partially a block diagram of another apparatus for removing biofilm from a wound site and reducing the likelihood of biofilm reformation thereafter.

An alternative instrument assembly 50 depicted in FIG. 2 has an operative tip or surface 52 and a suction channel 54 located between an outer surface 56 of an ultrasonic horn 58 and an inner surface 60 of a first or inner sheath 62. A second, outer, sheath 64 surrounds the first sheath 62 and defines therewith a second suction channel 66 for the evacuation of ambient air from a sizable region R' about the surgical site, exemplarily through a conical port element 68 at the distal end of the outer sheath 64. The two suction channels 54 and 66 may be connected to respective suction sources or vacuum generators 70 and 72 via respective valves 74 and 76 both actuatable by the operator via a control unit 78. Control unit 78 is tied to a control input (not separately designated) of an ultrasonic waveform generator 80 that is operatively connected to probe or horn 12 via an electromechanical transducer (not shown) such as a stack of piezoelectric crystals. Control unit 78 may be programmed to open valve 76 within a selectable time interval after the opening of valve 74 and the activation of waveform generator 80.

In a surgical procedure, instrument assembly 50 is manipulated to place the operative tip or surface 52 against patient's tissues PT' at a preselected surgical site SS'. During contact of the operative tip 52 with the patient's tissues PT', control unit 78 is operated to activate waveform generator 80, which generates an ultrasonic standing wave in probe or horn 58, to thereby fragment necrotic tissue and undesired organic material at the surgical site SS'. During the generating of the ultrasonic standing wave, a suction inlet 82 at a distal end of inner suction channel 54 is disposed proximate the surgical site SS' and a vacuum or negative pressure is applied by suction source 70 to the suction channel 54 via valve 74 to suck tissue debris and fragmented organic material from the surgical site SS' through the suction inlet 82. Conical port element 68 is disposed at a distance D2 from the surgical site SS'. During and/or after the generating of the ultrasonic standing wave and the fragmenting of tissue and material by instrument 50, vacuum generator 72 and valve 76 are actuated by control unit 78 to suck ambient air, as indicated by arrows 84, from region R' through suction port or cone 68. Suction inlet 82 is typically located a minimal distance, exemplarily between about 1 and about 5 mm, from tissues at the surgical site SS' while suction port 68 distance D2 is typically 2-6 cm from the surgical site SS'.

Outer sheath 64 may be temporarily fixed to inner sheath 62 via a quick-release lock 86 such as a set screw. Thus, the relative axial positions of sheaths 62 and 64 may be adjusted to change distance D2. Control unit 78 may be connected to suction sources or vacuum generators 70 and 72 for varying the power usage thereof and average magnitudes of the negative pressures generated thereby.

Figure 3:
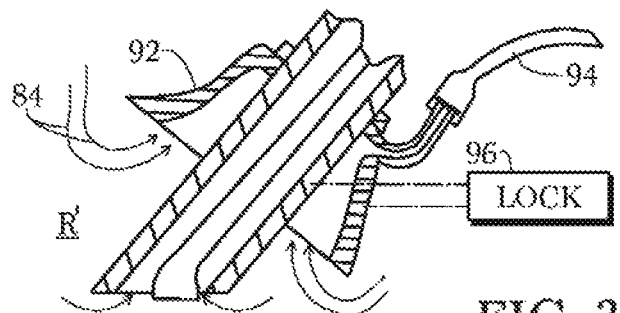
FIG. 3 is partially a schematic cross-sectional view and partially a block diagram of yet a further apparatus for removing biofilm from a wound site and reducing the likelihood of biofilm reformation thereafter.

FIG. 3 illustrates a modification of the instrument assembly 50 of FIG. 2. Instead of outer sheath 64, a suction nozzle 92 is attached to sheath 62. Nozzle 92 is connected to suction source or vacuum generator 72 via a reinforced hose 94. Nozzle 92 is removably, secured to sheath 62 via a locking element 96 such as a ring clamp or a set screw. The operation of modified instrument 90 is as discussed above.

The present method alternatively or additionally comprises placing an ultrasonic transducer 102 (see, e.g., FIGS. 4 and 5) in effective contact with a patient TP at least proximate a surgical site SI after terminating of a debridement or other tissue cleaning procedure and while the surgical site SI is free of discernible bacteria. Typically, transducer 102 is placed immediately after the surgical site SI has been cleaned of necrotic tissue and other undesirable debris and even prior to the removal of the patient TP from the operating room. After the placing of transducer 102 and while the transducer is in effective vibration-transmitting contact with the patient TP, an electrical energization waveform of an ultrasonic frequency is conducted from a waveform generator 104 to transducer 102 at least intermittently during a period of approximately one day or longer to reduce, if not prevent, biofilm formation on the patient at the surgical site SI and thereby facilitate a healing of the patient's tissue at the surgical site.

Figure 4:
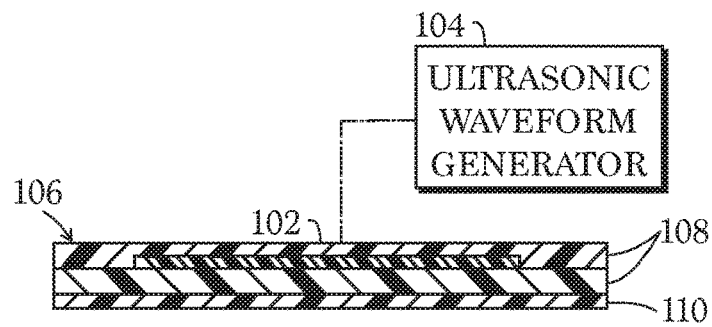
FIG. 4 is partially a schematic cross-sectional view and partially a block diagram of a device for attachment to a patient at a wound site, to reduce the likelihood of biofilm formation on the wound site.
Figure 5:
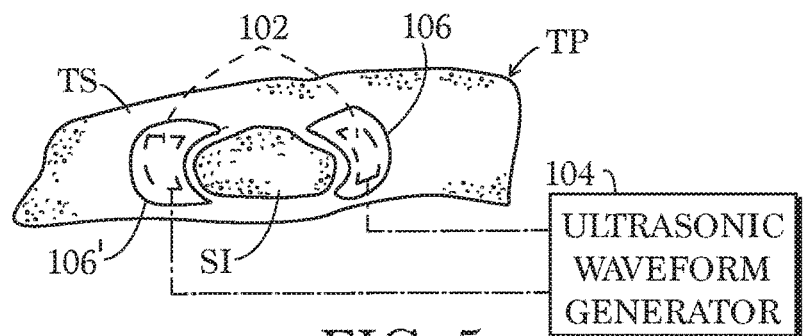
FIG. 5 is a schematic top plan view and partially a block diagram of the device of FIG. 4, in position and attached to a patient at a wound site on the patient.
Figure 6:
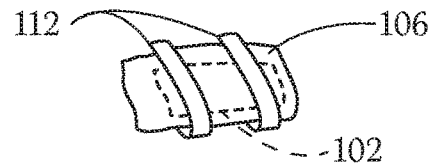
FIG. 6 is a schematic perspective view of another device for attachment to a patient at a wound site, to reduce the likelihood of biofilm formation.

As depicted in FIG. 4, transducer 102 may be affixed to a carrier pad 106, exemplarily sandwiched between layers 108 of a biocompatible and ultrasound transmitting material. The placing of transducer 102 on the patient TP preferably includes attaching pad 106 to the patient, for example, via an adhesive layer 110. As depicted in FIG. 5, pad 106 is disposed alone or together with one or more other carrier pads 106', on a tissue surface TS proximate surgical site SI. Alternatively, pad 106 may be placed directly over the surgical site SI shortly, if not immediately, after tissue removal is complete. In that case adhesive layer 110 may be omitted in favor of a layer of gel. The gel may be oxygenated and contain antibiotics. As depicted in FIG. 6, straps or bands 112 may be provided for securing the pad 106 to the patient TP.

Figure 7:
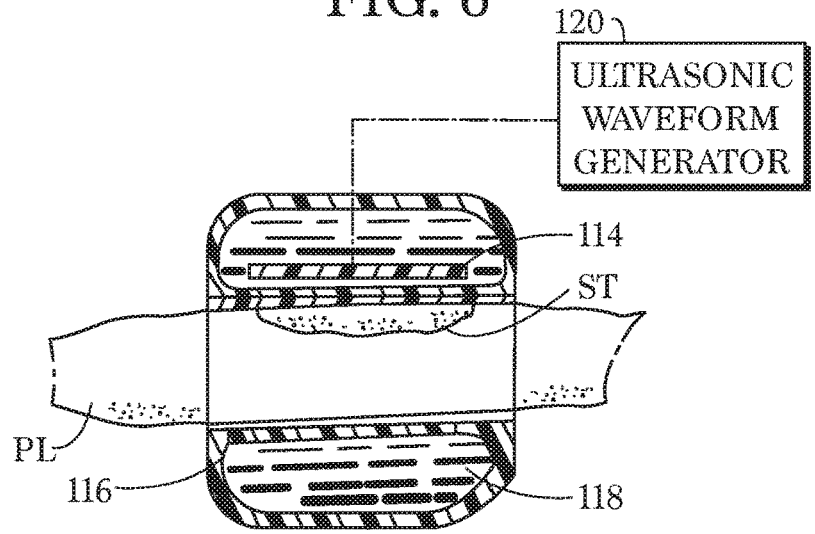
FIG. 7 is partially a schematic cross-sectional view and partially a block diagram of a device for attachment to a patient at a wound site, to reduce the likelihood of biofilm formation on the wound site, showing attachment of the device to a patient's limb.

Alternatively, as depicted in FIG. 7, an electromechanical, specifically, a piezoelectric, transducer 114 may be disposed inside a balloon or bladder 116 inflated with a gel or other medium 118 conducive to the effective transmission of ultrasonic pressure waves, the balloon or bladder being attached to a patient TP' over or adjacent a surgical site SI'. Balloon or bladder 116 is affixed to a patient, e.g., around an arm or leg PL, over or near a surgical site ST and an ultrasonic waveform generator 120 is activated to generate ultrasonic vibrations conducted into the patient's tissue to disrupt biofilm formation. Other transducer carriers and methods of attachment to the patient will occur to those skilled in the art.

A medical therapeutic method utilizing one or more of the transducer devices shown in FIGS. 4-7, first comprises cleaning surgical site SI or ST of necrotic tissue and undesired organic material, for instance via ultrasonic debridement and suction as discussed above with reference to FIGS. 1-3. Shortly thereafter, while the surgical site SI or ST is free of discernible bacteria, one places at least one ultrasonic transducer 102, 114 on the patient TP, TP' proximate or on the surgical site SI, ST, and thereafter, while the transducer is in effective vibration-transmitting contact with the patient TP, TP', conducting an electrical energization waveform of an ultrasonic frequency to the transducer 102, 114 at least intermittently during a period of approximately one day or longer. The waveform has frequency, amplitude and duration parameters selected to effectively reduce biofilm formation on the patient TP, TP' at the surgical site SI, ST and thereby facilitate a healing of the patient's tissue at the surgical site. The ultrasound generates a surface acoustic wave, exemplarily at 20 kHz, illustratively with an acoustic power output of 0.2-0.4 w/cm$^2$. The treatment period is long enough to enable healthy tissue formation. The placing of the transducer 102, 114 preferably includes removably attaching the transducer to the patient atop tissues at the surgical site SI, ST.

Figure 8:
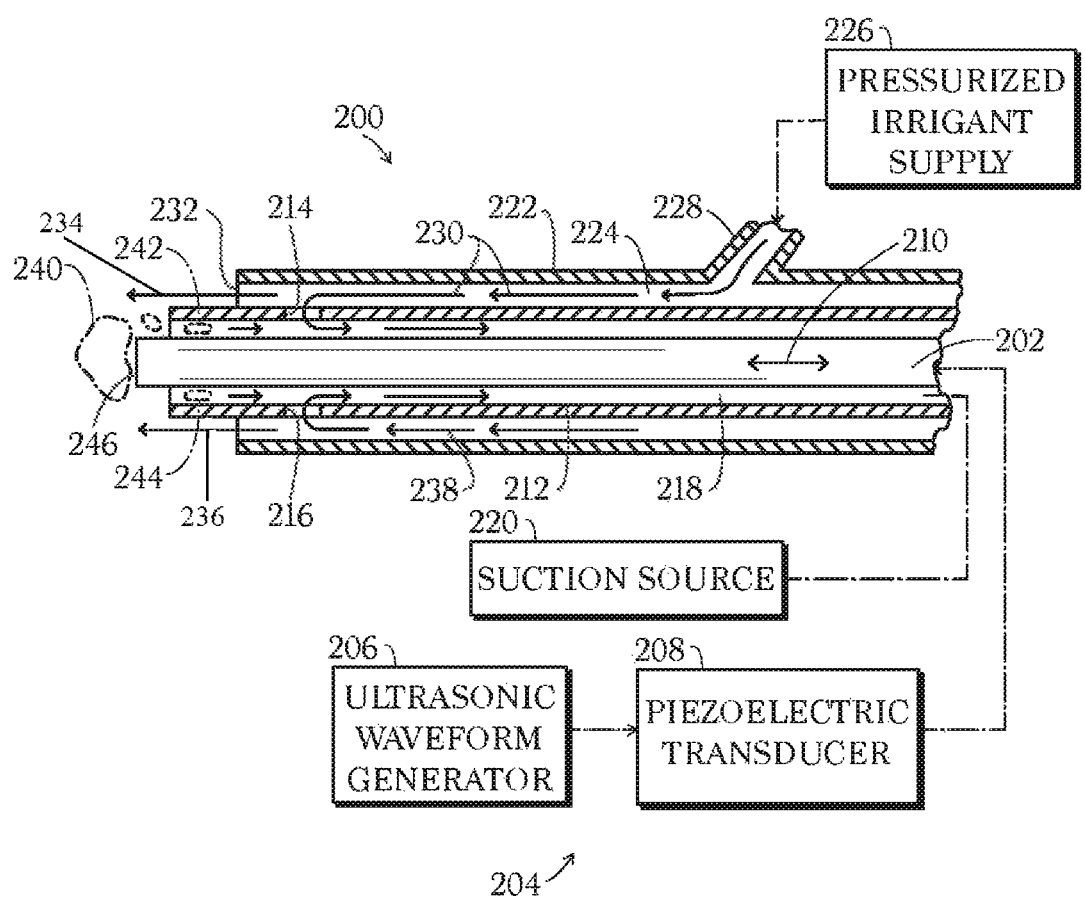
FIG. 8 is a schematic longitudinal cross-sectional view of a distal end portion of an ultrasonic instrument assembly that may be used in debridement and biofilm disruption.

As depicted in FIG. 8, an ultrasonic surgical device 200 comprises an ultrasonic probe 202 that is operatively connected to a source 204 of ultrasonic vibratory energy including an ultrasonic signal generator 206 and a stack of piezoelectric crystals 208 for vibrating at an ultrasonic frequency as symbolized by a double-headed arrow 210. Probe 202 extends longitudinally through an inner sheath 212 that is provided at a distal end region with one or more apertures 214, 216. Probe 202 and sheath 212 define an annular inner channel 218 that is connected at a proximal end of the instrument to a suction or vacuum source 220. An outer sheath 222 surrounds the inner sheath 212 and defines therewith an annular outer channel 224.

During use of the surgical device or assembly 200 of FIG. 8, irrigant flows from a supply 226 through an inlet port 228 and into outer channel 224, as indicated by arrows 230. The irrigant exits the outer channel 224 along two paths, firstly through a distal end opening 232, per arrows 234, 236, and secondly through apertures 214, 216 into inner channel 218 where the liquid or irrigant is drawn in a proximal action, as indicated by arrows 238, toward suction source 220.

At a surgical site 240, tissue fragments 242 and 244 are separated by ultrasonic vibration of a distal end surface 246 of probe 202 placed into contact with the surgical site. A vacuum underpressure at the distal end (not designated) of inner channel 218 draws tissue fragments 242, 244 into the inner channel, together with irrigant present at the surgical site 240 owing to outflow from outer channel 224 via distal end opening 232. Further irrigant entering inner channel 218 via apertures 214, 216 facilitates emulsion flow.

Device or assembly 200 is different from surgical aspirators where disrupted tissue is being aspirated through the center of a mostly cylindrical cannulated probe or small cross-section. In device 200 of FIG. 8, the dual irrigant capture scheme facilitates the delivery of sufficient liquid to ensure the occurrence of cavitation as well as to maintain safe temperature levels of both the probe 202 and the tissue at the surgical site 240. By capturing liquid via apertures 214, 216, before the irrigant can reach the surgical site 240, the device 200 reduces the volume of liquid that could be atomized by the probe 202.

The reduction of atomized irrigant is even more desirable in wound debridement procedures. This is due to the much larger size of the probe tip area normally used for large scale debridement, which is up to 80 times that of surgical aspirator probes, and also due to the larger volumes of irrigant required to maintain safe temperature levels in the tissue and probe.

Figure 9:
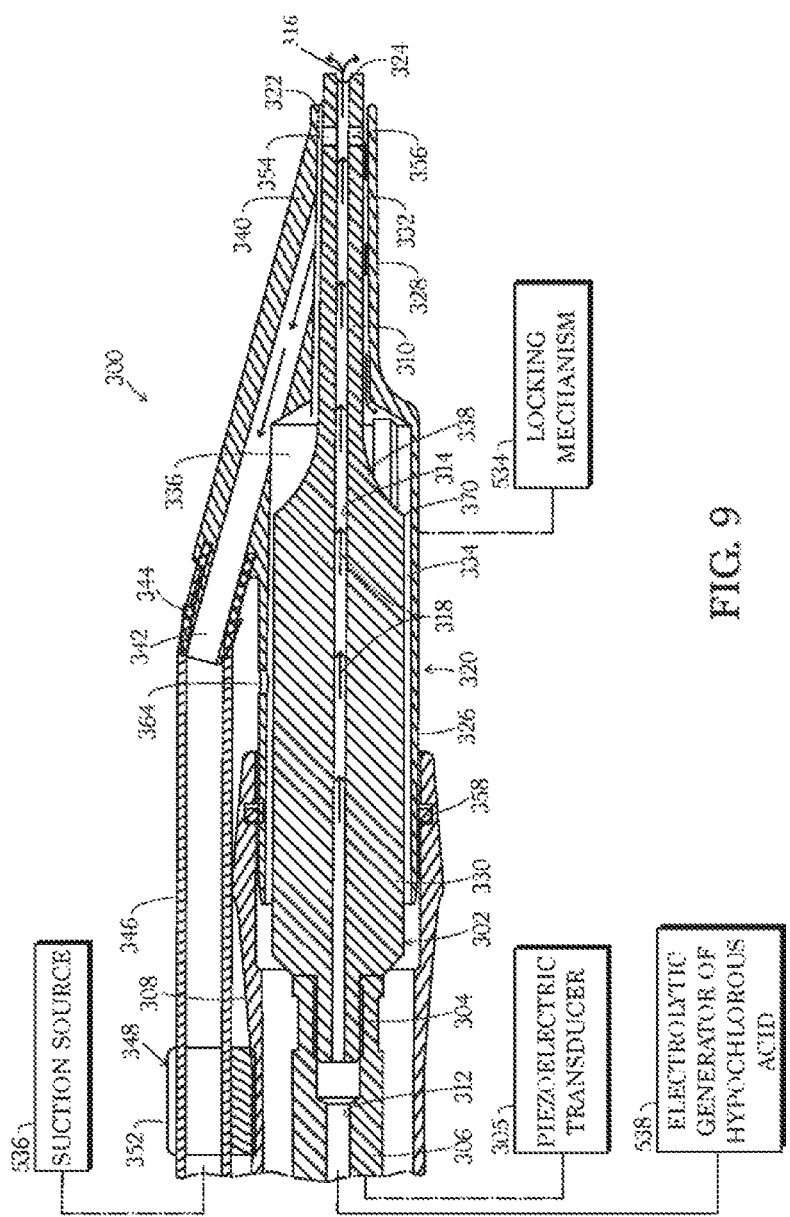
FIG. 9 is a partial longitudinal cross-sectional view of a device for debriding or removing biofilm from a wound site.
Figure 10:
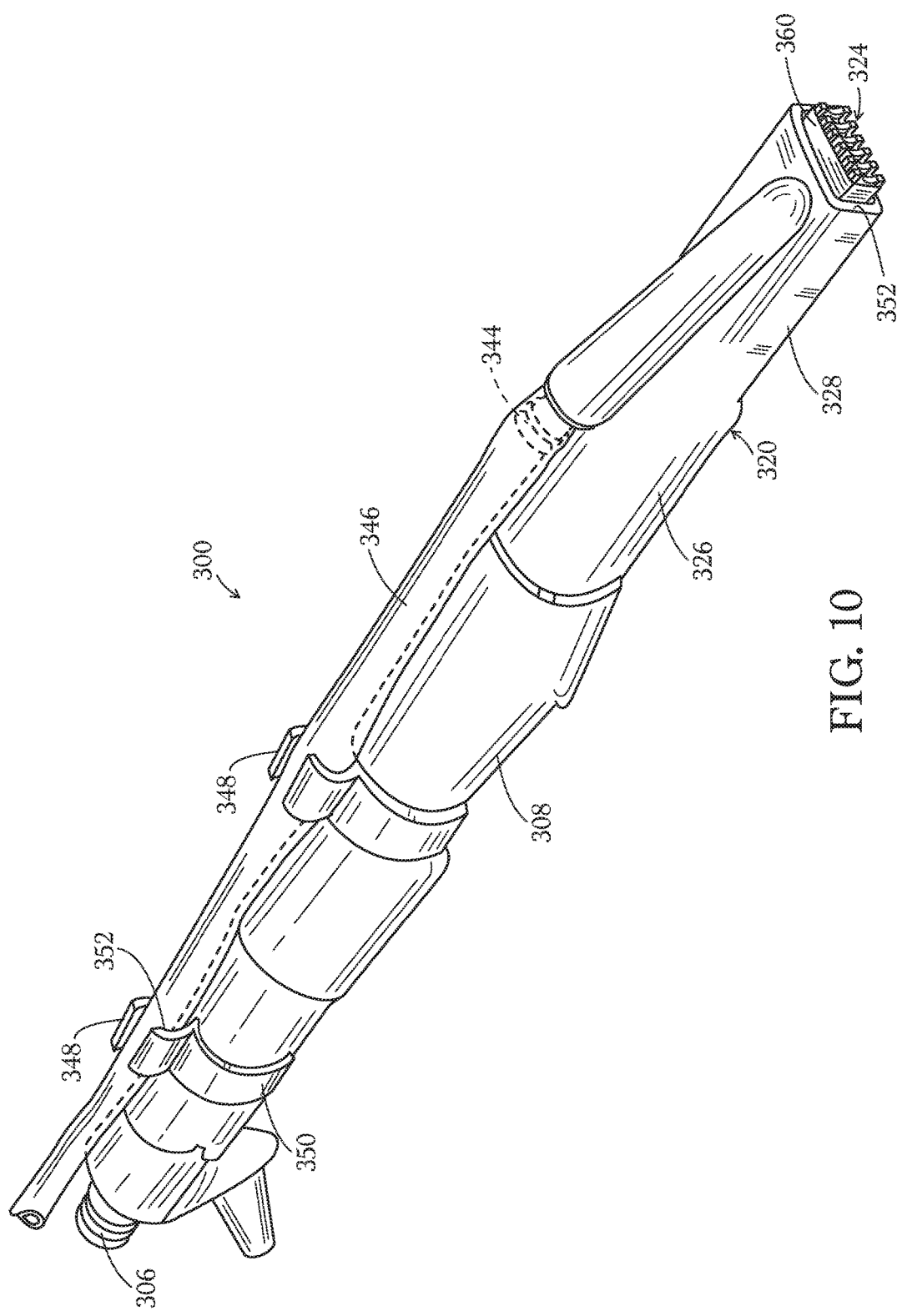
FIG. 10 is a schematic right side, top and front perspective view of the device of FIG. 9.
Figure 14:
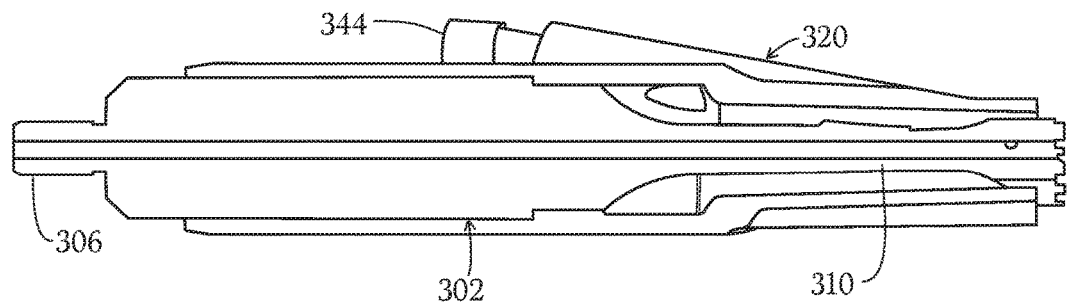
FIG. 14 is a partial cross-sectional view, similar to FIG. 9, taken along line XIV-XIV in FIG. 13.
Figure 15:
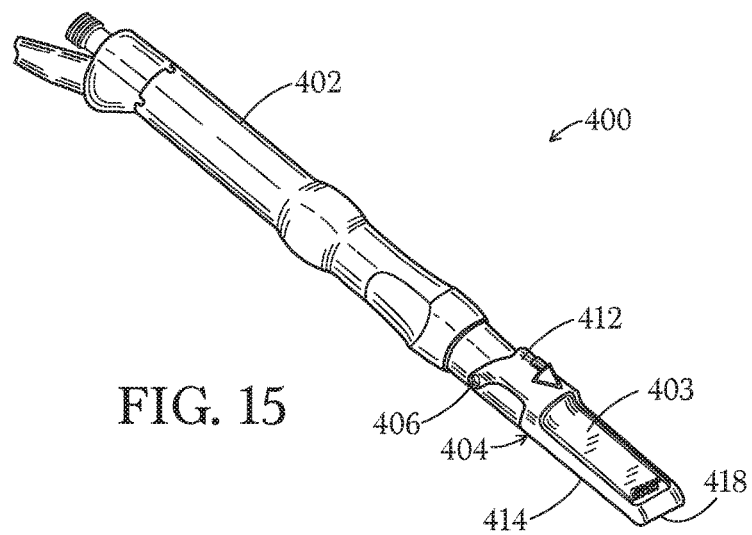
FIG. 15 is a right side, top and front perspective view of another device for debriding or removing biofilm from a wound site.
Figure 16:
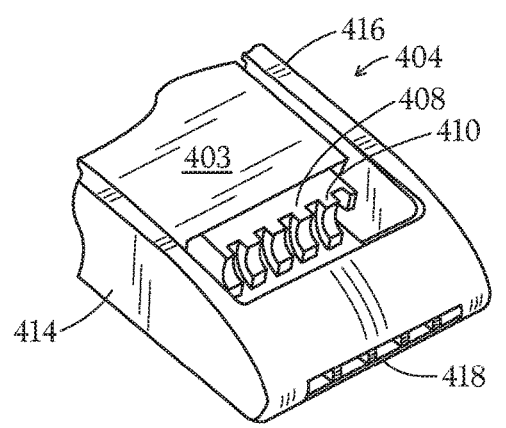
FIG. 16 is a partial right side, top and front perspective view, on an enlarged scale, of a distal tip portion of the device of FIG. 15.
Figure 17:
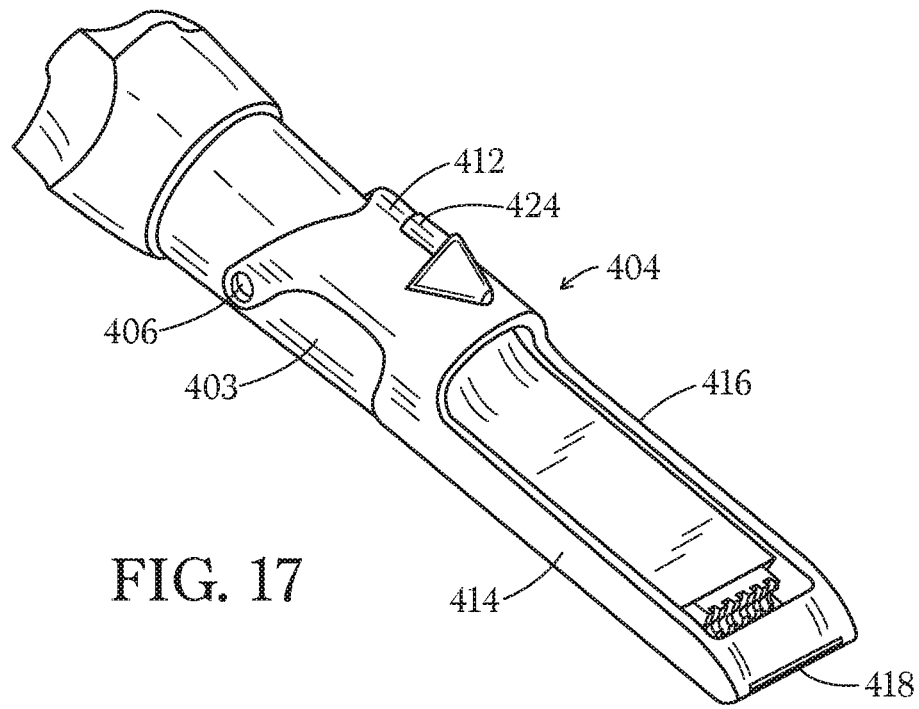
FIG. 17 is a partial right side, top and front perspective view, on an enlarged but intermediate scale, of a distal end portion of the device of FIGS. 15 and 16.

As depicted in FIGS. 9 and 10, a surgical device 300 for debriding or removing biofilm from a wound site comprises an ultrasonic probe 302 which is attached at a proximal end via threaded connector 304 to a driver 306 is operatively connected to a generator of vibratory energy, typically a piezoelectric transducer array 305. Both the driver 306 and the piezoelectric transducer 305 are located in a handpiece which has a cover or housing (not shown) connected to a casing 308. Probe 302 tapers down on a distal side to a distal end section 310. It is to be noted that the terms "horn" and "probe" are used synonymously.

Driver 306 and probe 302 are formed with mutually aligned axial channels or bores 312 and 314 that define a lumen (not separately designated) for the delivery of irrigant to a distal end aperture 316 in probe horn section 310, as indicated by flow arrows 318.

Surgical device or instrument 300 further includes a sheath or sleeve 320 that is shiftably mounted to casing 308 to vary a position of a distal tip 322 of the sheath relative to a distal tip or end face 324 of probe 302. Sheath 320 includes a cylindrical rear section 326 and a rectangularly prismatic forward section 328, which correspond geometrically to cross-sections of horn 310 and a proximal portion 330 of probe, 302, respectively. (Other cross-sectional shapes are possible. For instance, forward section 328 could be oval or circular, where horn 328 has an oval or circular cross-section.) Sheath 320 may be rigid in its entirety or, alternatively, at least forward section 328 may be semi-rigid or flexible, to better conform to target tissue topography.

Together with an outer surface (not designated) of probe horn 310, forward sheath section 328 defines a forward or distal channel or conduit 332, which is rectangular in cross-section. Together with an outer surface (not designated) of proximal probe portion 330, rear sheath section 326 defines a rearward or proximal channel or conduit 334, which is circular in cross-section. At a distal end, rearward channel 334 expands to an enlarged space 336 owing to the tapering of the probe at 338.

Sheath 320 is provided with an arm 340 that is connected at a forward or distal end to forward section 326 and is angled outwardly at a proximal side. Sheath arm 340 includes a main aspiration channel 342 that communicates at a distal end with forward channel 332. At a more proximal location, aspiration channel 342 of arm 340 communicates with rearward channel 334 and more particularly with enlarged space 336. At a proximal end, arm 340 is provided with an undercut connector port 344 which receives a resilient aspiration tube 346 in a friction fit. Aspiration tube 346 is fastened to casing 308 via a pair of clips 348 each formed with a pair of slotted annular rings 350 and 352 for receiving casing 308 and aspiration tube 346, respectively.

At a forward or distal end, probe horn 310 is formed with one or more apertures or cross-bores 354 and 356 that communicate on an inner side with channel or lumen 314 and on an outer side with forward channel 332. At a rear end, rear section 326 of sheath 320 is inserted between proximal probe portion 330 and a distal end of casing 308. An O-ring seal 358 is provided between casing 308 and an outer surface of sheath rear section 326.

A distal end of horn section 310 is formed into a probe head 360 that is extended in a traverse dimension, orthogonally to a longitudinal axis of the probe 302. Head 360 may particularly take a form disclosed in U.S. patent application Ser. No. 14/172,566, Publication No. 2015/0216549, the disclosure of which is incorporated by reference herein. In particular, head 360 includes a plurality of teeth 362 arranged in two mutually parallel rows along opposing edges or sides of the distal end face 324 of the probe head.

As indicated above, sheath 320 is slidable or longitudinally shiftable relative to probe 302 so as to be continuously adjustable as to axial or longitudinal position relative to probe head 360 anywhere from a fully extended position, where the distal tip 322 of sheath 320 is essentially coplanar with the distal end face 324 of probe head 360, to a retracted position where at least the teeth 362 of probe head 360 are fully exposed. O-ring 358 enables the adjustable positioning of sheath 320.

Apertures or cross-bores 354 and 356 serves as bypass holes, regardless of the relative longitudinal positioning of sheath 320 and probe 302. A vacuum under-pressure applied to the internal spaces of sheath 320, i.e., aspiration channel 342, forward channel 332, and rearward channel 334, by a suction source (not shown) enables the capturing and removal of most of the irrigant that is delivered through central channel 314 (flow arrows 318). Accumulation of irrigant within sheath 320, especially when the device is used in a predominantly vertical orientation, is prevented by the provision of two suction pathways, namely, between aspiration channel 342 and each of the forward channel 332 and rearward channel 334. Irrigant not captured via a distal pathway is captured in a proximal pathway.

Where tissue fragments are small enough to be aspirated through the gap between the probe 302 and the sheath 320, clogging is prevented by designing the aspiration pathway of channel 324 to gradually increase in cross-sectional area from the probe-sheath gap at the distal end of the instrument all the way to the aspiration line. A vent port 364 may be provided in the rear sheath section 326 to reduce the magnitude of vacuum-generated pull force acting on the tissue which is driven towards and into the probe-sheath gap during debridement.

Matching or cooperating features 366 and 368 are respectively disposed on the outer side of the probe 302 and the inside of rear sheath section 326, in close proximity to a nodal plane or the probe, to facilitate probe-sheath alignment. This minimizes the chances of a probe-sheath contact at the points of maximum vibratory motion (antinodes), particularly at end face 324 of probe head 360. Due to their placement at a location of minimal vibratory displacement, e.g., the junction 370 between cylindrical probe portion 330 and tapering probe section 338, the alignment features 366 and 368 allow for the probe-sheath contact necessary for preventing or minimizing the unwanted interaction in the area of maximum vibratory displacement.

As depicted in FIGS. 15-18, another ultrasonic surgical device 400 for debriding or removing biofilm from a wound site comprises a handpiece 402 provided at a distal end with a sheath 403 and a suction or evacuation attachment 404 swingably attached to the sheath at pivot pins 406 (only one shown). An ultrasonic probe is disposed inside handpiece 402 and sheath 403 and terminates and a distal end in a head 408 formed with crenulations or teeth 410.

Figure 18:
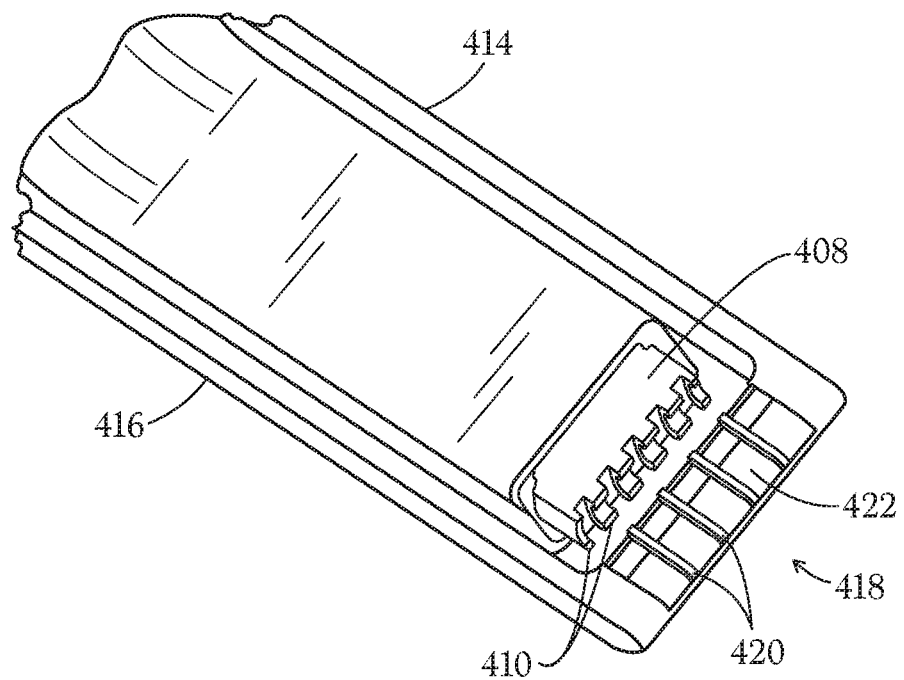
FIG. 18 is a left side, bottom, and front perspective view, on an enlarged scale, of the device of FIGS. 15-17.

Suction attachment 404 includes a body portion 412 at a proximal end and a pair of hollow arms 414, 416 extending in a distal direction from the body portion. Arms 414 and 416 are joined to one another at their distal end by a cross-piece 418 serving as a suction head. As shown in FIG. 18, suction head 418 is formed on a lower side with a plurality of longitudinally extending runners or ribs 420 and a recess 422, which is bridged by the runners or ribs and which communicated with aspiration channels (not shown) in the hollow arms 414, 416. Body portion 412 is provided with a port connector 424 to which an aspiration tube (like tube 346) is attached. Liquid irrigant is guided to an outlet port (not shown) in probe head 408 via a channel (not shown) in the probe. The irrigant, together with tissue fragments and other surgically generated debris, is drawn from the surgical site via suction attachment 404. More particularly, during a debridement operation, suction head 418 is placed in essential contact with the tissue at the surgical site. Irrigant and tissue debris are collected via recess 422 and guided through arms 414 and 416 and out through port connector 424.

The pivotable mounting of suction attachment 404 enables suction head 418 and particularly recess 422 to remain juxtaposed to a tissue surface even as the rest of the instrument particularly handpiece 402, sheath 403 and the probe are tilted to assume different angles relative to a normal to the tissue surface.

Figure 19:
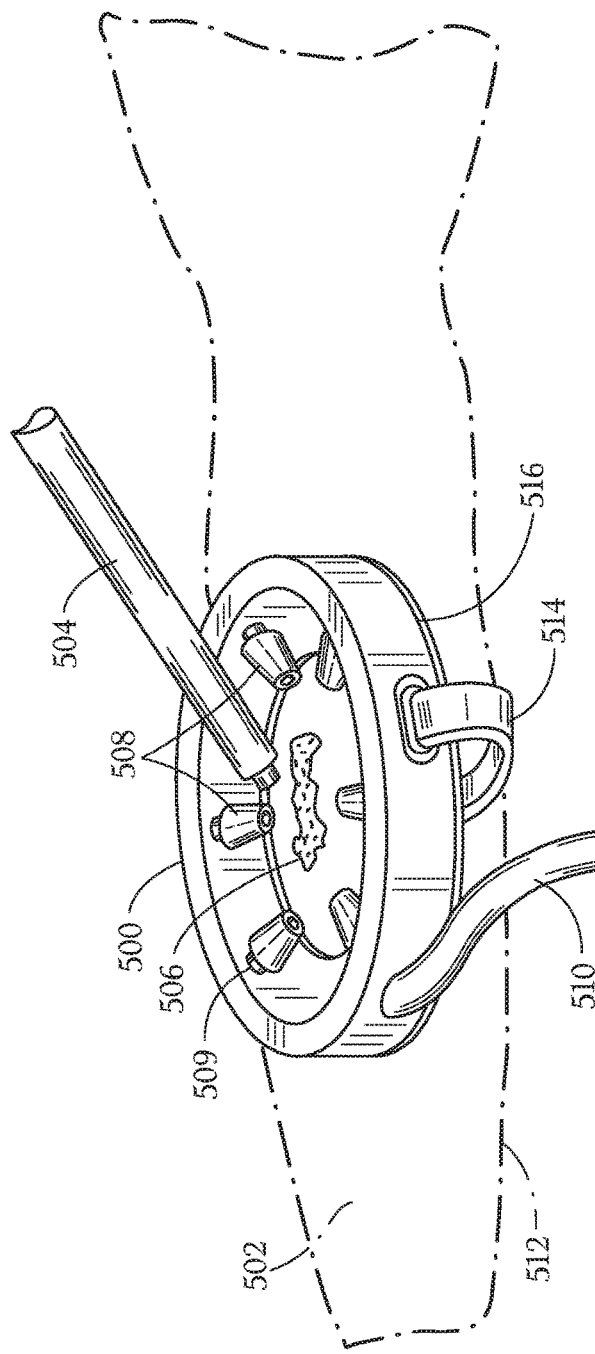
FIG. 19 is a schematic perspective view of a suction device, in place around a surgical site.

FIG. 19 shows a suction device 500 in the form of a ring that is placed on a tissue surface 502 for purposes of removing airborne particles generated by use of an ultrasonic instrument 504 on tissue at a surgical site 506. Ring 500 is provided along an inner cylindrical surface with a plurality of spaced suction ports 508. Ports 508 may be tiltably mounted to the ring 500, e.g., via universal joints that have joint balls 509 that are perforated. Ring 500 is at least partially hollow so that suction ports 508 may communicate via a hose 510 with a suction source (not shown). Ring 500 may be attached to a patient, e.g., to a limb 512, via one or more of various coupling devices, such as a strap 514 with buckles or hook-and-loop fabric fasteners, or an adhesive layer 516.

FIGS. 20-23 depict modifications to the instrument assembly of FIGS. 9-14, which facilitates use of the instrument to clean biofilm from hard surfaces such as those of a prosthesis or a surgical instrument. The above disclosure with reference to FIGS. 9-14 is hereby repeated with respect to the modifications of FIGS. 20-23 and incorporated therein. Selected reference numerals in FIGS. 9-14 are used in FIGS. 20-23 to designate the same or like structures.

As described above with reference to FIGS. 9-14, ultrasonic probe 302 has operative tip or end face 324 and an axial or longitudinal channel 314 for the delivery of irrigant to distal end aperture 316 in probe horn section 310, as indicated by flow arrows 318. Electromechanical transducer 305 is operatively connected to probe 302 for generating an ultrasonic standing wave therein to vibrate operative tip 324 at ultrasonic frequency. Sheath or sleeve 320 is disposed about probe 302 and defines channel 332, 334, 336, 342 (FIG. 9) outside the probe. Channel 332, 334, 336, 342 has at least a first port 520 in a region about a distal end of probe 302, proximate the operative tip 324. Port 520 is specifically a gap between an inner surface (not designated) of sheath or sleeve 320 and an outer surface (not designated) of probe 302 in the region of the distal end face or operative tip 324 thereof. Sheath or sleeve 320 has an operative configuration wherein a distal end portion 522 of the sheath or sleeve extends distally beyond operative tip or end face 324 of probe 302 to define or enclose an ultrasound coupling space or antechamber 524 between operative tip 324 and a target surface TS.

Figure 22:
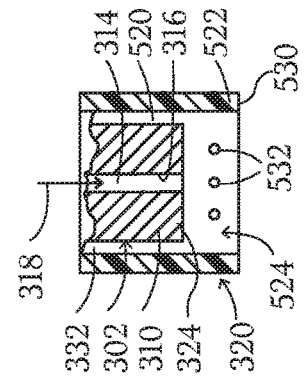
FIG. 22 is a diagrammatic longitudinal cross-sectional view of a distal end of another ultrasonic surgical instrument assembly that is an alternative modification of the device of FIGS. 9-14.
Figure 21:
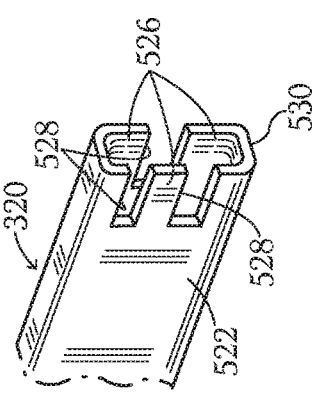
FIG. 21 is a diagrammatic perspective view of the modification of FIG. 20.
Figure 20:
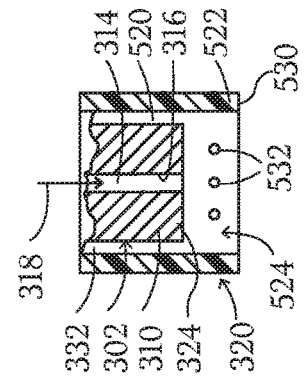
FIG. 20 is a diagrammatic longitudinal cross-sectional view of a distal end of an ultrasonic surgical instrument assembly that is a modification of the device of FIGS. 9-14.
Figure 23:
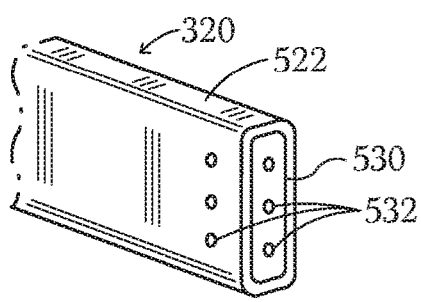
FIG. 23 is a diagrammatic perspective view of the modification of FIG. 22.

As depicted in FIGS. 20 and 21, the distal end portion of sheath or sleeve 320 may be formed with a plurality of longitudinally extending fingers 526 separated by one or more gaps or spaces 528. Gaps or spaces 528 are slots in the distal end portion of sheath or sleeve 320 extending rearwardly from a rounded rectangular distal edge 530. As depicted in FIGS. 22 and 23, the distal end portion of sheath or sleeve 320 may be alternatively formed with one or more apertures 532 in a sidewall (not separately labeled) of the sheath or sleeve, the aperture(s) 532 being spaced from distal edge or tip 530 of the sheath or sleeve. Gaps 528 and apertures 532 enable an ingress of air into coupling space or antechamber 524 for the removal of the coupling medium (irrigant) and collected detritus as a slurry via suction or inlet port 520. This operation mode of sheath or sleeve 520 serves to prevent or reduce the egress of atomized irrigant and pathogenic particles from the treatment zone.

The treatment zone may be defined as the area of the target surface surrounded by or bounded by distal edge 530 of the sheath or sleeve 520. The treatment zone typically moves about a larger surface during debridement of organic tissues at a wound site or biofilm reduction at a wound site or on a hard surface. The rate of irrigant flow distally through probe channel 314 and the associate rate of slurry removal via suction channel 332, 334, 336, 342 is preferably sufficiently great not only to remove the biofilm particles and pathogenic components from the treatment zone but also to cool probe 302 and the treatment site, at least in the case of debridement of a wound bed or tissue injury site.

During the use of the instrument, irrigant delivered to the distal end of probe 302 accumulates to act as a coupling medium in the coupling space or antechamber 524. Ultrasonic compression waves are transmitted through the coupling medium irrigant from the probe tip or end face 324 to generate disruptive cavitation or other micron-sized mechanical and thermal disturbances at the target surface TS.

Antechamber or enclosure 524, which is defined or formed by the distal end portion of sheath or sleeve 520, the operative tip or end face 423 of probe 302, and the target surface TS, functions in part to ensure a separation of the operative probe tip 324 from the target surface TS. Antechamber or enclosure 524 also functions to enable effective ultrasound pressure wave coupling, owing to the containment of liquid irrigant in the antechamber or enclosure. Antechamber or enclosure also serves to reduce spray or atomized detritus and contain the detritus and potential pathogenic particles for removal via the suction channel 332, 334, 336, 342 in the sheath or sleeve 320.

Figure 24:
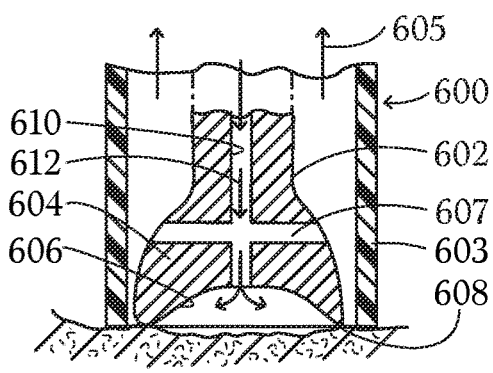
FIG. 24 is a diagrammatic longitudinal cross-sectional view of a distal end of an ultrasonic surgical probe that is a modification of the probe of FIGS. 9-14.

As shown in FIG. 24, an ultrasonic instrument 600 for use in biofilm removal, particularly from target tissue TT' on a patient, includes a probe 602 longitudinally traversing a sheath or sleeve 603. Probe 602 includes a head 604 with a bowl-shaped concavity or recess 606 surrounded by a distal lip of rim 608 of head 604. During use of the probe 602 to remove biofilm, rim 608 is typically the only part of the probe that comes into actual contact with target tissue TT'. During a biofilm removal operation, irrigant flows under pressure through a channel 610 in probe 602, as indicated by arrows 612, and fills cavity or recess 606 to form a pool. The irrigant and potential contaminants as well as tissue and biofilm fragments are removed, as indicated by arrows 605, via suction applied via sheath or sleeve 603 (see discussion above). Probe 602 may be provided exemplarily in head 604 with one, two or more bypass ports or bores 607 that communicate on an inner side with channel 610 and on an outer side with sheath or sleeve 603 and more particularly with a lumen (not separately designated) of sheath or sleeve 603. Ports or bores 607 are oriented generally transversely to channel 610 and concomitantly perpendicularly to a longitudinal axis (not shown) of probe 602.

Figure 25:
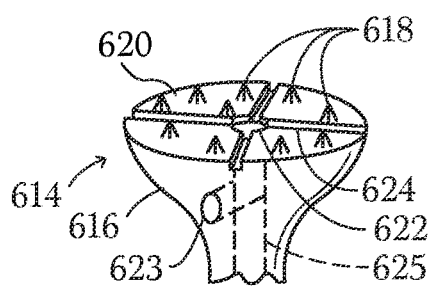
FIG. 25 is a diagrammatic side elevational view of a distal end of another ultrasonic surgical probe that is a modification of the probe of FIGS. 9-14.

As illustrated in FIG. 25, another ultrasonic probe 614 for use in biofilm removal includes a probe head 616 having an array of projections or raised elements 618 mutually spaced on an end face 620 of the probe head. Projections or raised elements 618 may exemplarily take a conical, pyramidal or pointed tooth shape. An irrigation output port 622 typically, but not necessarily, at the center of end face 620 communicates with a plurality of radiating grooves 624 that distribute the irrigant from port 622 across end face 620. Projections or raised elements 618 are distributed across the entire end face 620 between outlet port 618 and an edge or periphery of the end face. One or more bypass ports or bores 623 may be provided in probe 614, exemplarily in probe head 616. Ports or bores 623 extend from a channel 625 in probe 614 to an outer surface (not separately designated) thereof. Probe 614 is typically used with a sheath or sleeve (not shown) as discussed hereinabove, for instance with respect to FIG. 24.

Figure 26:
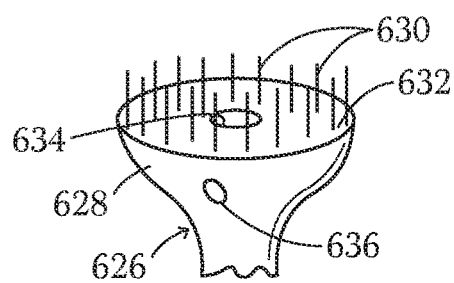
FIG. 26 is a diagrammatic side elevational view of a distal end of yet another ultrasonic surgical probe that is a modification of the probe of FIGS. 9-14.

As depicted in FIG. 26, a further ultrasonic probe 626 for use in biofilm removal both in vivo from a tissue site and also, alternatively, from a surface of a prosthesis or a surgical instrument, includes a probe head 628 having an array of metallic hairs or filaments 630 mutually spaced on an end face 632 of the probe head. An irrigation output port 634 is typically formed at the center of end face 632. Head 628 with filaments 620 is an ultrasonic brush head, where the flexibility of the filaments makes the probe 626 compatible for removal of biofilm from hard surfaces. Hairs or filaments 630 are distributed across the entire end face 632 between outlet port 634 and an edge or periphery of the end face. One or more bypass ports or bores 636 may be provided in probe 626, exemplarily in probe head 628. Ports or bores 636 extend from a channel (not shown) in probe 626 to an outer surface (not separately designated) thereof. Probe 626 is typically used with a sheath or sleeve (not shown) as discussed hereinabove, for instance with respect to FIG. 24.

As described herein above with reference to FIGS. 9-14, sheath or sleeve 320 is longitudinally slidable relative to probe 302 to shift between a distal or extended position (FIGS. 20-23) in the operative configuration and a proximal or retracted position. In the distal-most or extended position of the sheath or sleeve 320, the probe head particularly including operative tip or end face 324 is covered while in a proximal-most position of the sheath or sleeve at least a portion of the probe head necessarily including operative tip or end face 324 is exposed. The instrument may be provided with a locking mechanism 534 (FIG. 9), such as a set screw, a clamp, or a friction fit, which holds the sheath or sleeve 320 in either the extended position or the retracted position, and optionally any position therebetween. Such a locking mechanism 534 is preferably located at a vibration node of the probe 302, so that the lock does not affect the generation of a standing wave in the probe, as is well known in the art.

It is seen from FIG. 9 that probe 302 and sheath or sleeve 320 define a first space or channel 332 and a second space or channel 336 both generally laterally or to the side of the probe, and particularly surrounding the same. The second space or channel 336 is located proximally of the first space or channel 332 and has a larger transverse cross-sectional area, in a plane orthogonal to an axis of the probe 302, than the first space or channel 336. As discussed above (FIG. 9) probe 302 may be provided at or in a distal end portion with at least one aperture 356 spaced from the outlet and communicating with the first space or channel 332. Sheath or sleeve 320 is provided with an aspiration arm 340 having an aspiration channel 342 communicating with the first space or channel 332 and the second space or channel 336.

The ultrasonic debridement instrument 300 as modified per FIGS. 20-23 is manipulated to place the distal tip or edge 530 of sheath or sleeve 320 against a target surface TS such as a wound site or a surface of a prosthesis needing cleaning. The instrument 300 is manipulated to place the sheath or sleeve so that it extends in part distally of the operative tip or end face 324 of the probe 302, as shown in FIGS. 20-23 and serves in part to maintain or create a spacing between the probe's operative tip and the target surface TS. The spacing or distance between operative tip or end face 324 and target surface TS must be large enough, for hard surfaces TS, to avoid contact between the probe tip and the hard surface but cannot be so large as to damp the ultrasonic vibration energy so as to render that energy ineffective in the disruption and fragmentation of biofilm adhering to the hard surface. Typically, the spacing or height or the antechamber or coupling enclosure 524 is between about 100 microns and several millimeters. The manipulating of the instrument 300 to place the distal tip or edge 530 of sheath or sleeve 320 against the target surface TS inherently positions the operative tip 324 or the probe at a desired distance from the target surface.

During contact of the distal tip or edge 530 of sheath or sleeve 320 with the target surface TS, one feeds an irrigation fluid (flow arrows 318) through channel 314 in probe 302 to the antechamber or coupling enclosure 524. Also during contact of the distal tip or edge 530 of the sheath or sleeve 320 with the target surface TS, an ultrasonic standing wave is generated in the probe 302 to vibrate the operative tip or end face 524 thereof and thereby fragment undesired material at or on the target surface. During the generating of the ultrasonic standing wave, vacuum or negative pressure is applied to the second channel by a vacuum generator or suction source 536 (FIG. 9) to remove fluid from the target surface TS.

Preferably, the irrigation fluid (318) includes a disinfectant or biocide such as hypochlorous acid and/or metal ion hypochlorite. This disinfectant or biocide is advantageously generated on site, at or immediately prior to the treatment by ultrasound, thereby ensuring an effective concentration of the hypochlorous acid. The hypochlorous acid and/or metal ion hypochlorite may be produced from a sterile saline solution by an electrolytic generator 538 (FIG. 9) as described in U.S. Patent Application Publication No. 2016/0222526 the disclosure of which is hereby incorporated by reference.

As discussed above, sheath or sleeve 320 is slidably mounted so that the sheath or sleeve is longitudinally shiftable relative to probe 302. Sheath or sleeve 320 is shifted in a distal direction along the instrument prior to the manipulating of the instrument to place the distal tip or edge 530 of the sheath or sleeve against the target surface TS. Variability in the longitudinal position of sheath or sleeve 320 relative to probe 302 enables the user to adjust the height of the coupling space or antechamber 524 between the operative surface 324 of probe 302 and the target surface TS. The height may be close to zero, in which case the operative tip 324 of probe 302 may be placed in contact or near contact with a target surface TS such as organic tissue at a site of a patient wound or injury. This option is described above with reference to FIGS. 9-14.

Typically the second channel 332, 334, 336, 342 is located between sheath or sleeve 320 and probe 302. The method may also comprise shifting sheath or sleeve 320 in a proximal direction after the generating of the ultrasonic standing wave and thereafter applying a vacuum or negative pressure to the suction channel 332, 334, 336, 342 to suck ambient air into and through the suction channel.

The method described hereinabove is advantageous in cleaning biofilm from a hard target surface TS such as a surface of a prosthesis. The cleaning of the prosthesis may be effectuated in vivo, where open surgery uncovers at least a portion of a prosthesis, or ex vivo, where the prosthesis has been temporarily removed from the patient.

Where the present method is used to clean a hard target surface, the spacing of the vibrating operative probe surface 324 from the target surface TS by the distally extended or projecting sheath 320 prevents high frequency impact of the metal or alloy probe with a prosthesis that is also typically made of a metal or alloy. Thus the likelihood of inadvertent damage to the prosthesis is reduced if not eliminated, while resonance operation of the probe is maintained.

The target surface may alternatively be a surface of a surgical instrument.

The present invention provides an additional benefit which applies both where the target surface TS is patient tissue and where the target surface is an instrument or prosthesis surface. That is an enhanced effectiveness in reducing the incidence of airborne pathogens. The atomization and dispersal or liquid from the treatment site is controlled or limited by a barrier formed by the distal end of the sheath or sleeve 320, in combination with the suction applied to the coupling space or antechamber 524. Sheath or sleeve 320 encloses the treatment site and thus contains fragmented biofilm and/or tissue for immediate removal through the suction channel 332, 334, 336, 342 of the instrument. The distal end portion of the sheath or sleeve 320 is provide with openings, i.e., gaps 528 or apertures 532, that are limited in cross-sectional area, just to permit the ingress or air for enabling effective suctioning of the slurry produced at the treatment site.

Although the invention has been described in terms of particular embodiments and applications, one of ordinary skill in the art, in light of this teaching, can generate additional embodiments and modifications without departing from the spirit of or exceeding the scope of the claimed invention. Moreover, the phase shift might be varying, for instance, where the vibration modes are of different frequencies. Accordingly, it is to be understood that the drawings and descriptions herein are proffered by way of example to facilitate comprehension of the invention and should not be construed to limit the scope thereof.

What is claimed is:

1. A medical therapeutic method comprising:
   providing an ultrasonic debridement instrument having a probe with an operative tip and a first channel, said instrument including a sheath or sleeve with a distal tip, said sheath or sleeve defining a second channel extending outside said probe, said second channel having an inlet proximate said distal tip;
   manipulating said instrument to place said distal tip against a target surface, said sheath or sleeve extending in part distally of said operative tip and serving in part to maintain a spacing between said operative tip and the target surface, whereby the manipulating of said instrument to place said distal tip against the target surface inherently positions said operative tip at a distance from the target surface and defines or encloses an ultrasound coupling space or antechamber between said operative tip and the target surface;
   during contact of said distal tip with the target surface, feeding an irrigation fluid through said first channel to said ultrasound coupling space or antechamber between said operative tip and the target surface;
   also during contact of said distal tip with the target surface, generating an ultrasonic standing wave in said probe to vibrate said operative tip and thereby fragment undesired material at or on the target surface; and
   during the generating of said ultrasonic standing wave, applying vacuum or negative pressure to said second channel to remove fluid from the target surface.

2. The method defined in claim 1 wherein said sheath or sleeve is longitudinally shiftable relative to said probe, further comprising shifting said sheath or sleeve in a proximal direction along said instrument prior to the manipulating of said instrument to place said distal tip against the target surface.

3. The method defined in claim 2 wherein said second channel is located between said sheath or sleeve and said probe of said instrument, further comprising: shifting said sheath or sleeve in a proximal direction after the generating of said ultrasonic standing wave; and thereafter applying a vacuum or negative pressure to said second channel to suck ambient air into and through said second channel.

4. The method defined in claim 1 wherein the target surface is tissue of a patient.

5. The method defined in claim 1 wherein said irrigation fluid includes hypochlorous acid, further comprising electrolytically generating the hypochorous acid on site.

6. A medical therapeutic method comprising:
   providing an ultrasonic debridement instrument having aerobe with an operative tip and a first channel, said instrument including a sheath or sleeve with a distal tip, said sheath or sleeve defining a second channel extending outside said probe, said second channel having an inlet proximate said distal tip;
   manipulating said instrument to place said distal tip against a target surface, said sheath or sleeve extending in part distally of said operative tip and serving in part to maintain a spacing between said operative tip and the target surface, whereby the manipulating of said instrument to place said distal tip against the target surface inherently positions said operative tip at a distance from the target surface;
   during contact of said distal tip with the target surface, feeding an irrigation fluid through said first channel to a region between said operative tip and the target surface;
   also during contact of said distal tip with the target surface, generating an ultrasonic standing wave in said probe to vibrate said operative tip and thereby fragment undesired material at or on the target surface; and
   during the generating of said ultrasonic standing wave, applying vacuum or negative pressure to said second channel to remove fluid from the target surface,
   wherein the target surface is a hard surface.

7. The method defined in claim 6 wherein the target surface is a surface of a prosthesis.

8. The method defined in claim 6 wherein the target surface is a surface of a surgical instrument.

9. A surgical device comprising:
   an ultrasonic probe having an operative tip and a first channel extending longitudinally therein;
   an electromechanical transducer operatively connected to said probe for generating an ultrasonic standing wave in said probe to vibrate said operative tip at ultrasonic frequency; and
   at least one sheath or sleeve disposed about said probe and defining a second channel outside said probe, said second channel having at least a first port in a region about a distal end of said probe, proximate said operative tip, said sheath or sleeve having an operative configuration wherein a distal end portion of said sheath or sleeve extends distally beyond said operative tip of said probe to define an ultrasound coupling space between said operative tip and a target surface.

10. The surgical device defined in claim 9 wherein said sheath or sleeve is longitudinally slidable relative to said probe to shift between a distal position in said operative configuration and a proximal position.

11. The surgical device defined in claim 10 wherein said probe and said sheath or sleeve define a first space or channel and a second space or channel, said second space or channel being located proximally of said first space or channel and having a larger transverse cross-sectional area, in a plane orthogonal to an axis of said probe, than said first space or channel.

12. The surgical device defined in claim 11 wherein said probe is provided at or in a distal end portion with at least one aperture communicating with said first space or channel, said sheath being provided with an aspiration arm having an aspiration channel communicating with said first space or channel and said second space or channel.

13. The surgical device defined in claim 12 wherein said probe includes a proximal body section, a smaller-diameter horn section, and a probe head, the horn section extending distally of said body section, said head being formed at a distal end of said horn section.

14. The surgical device defined in claim 10 wherein said sheath or sleeve is configured to shift between a distal-most position wherein said probe head is covered and a proximal-most position wherein at least a portion of said probe head is exposed.

15. The surgical device defined in claim 9 wherein said distal end portion of said sheath or sleeve is formed with a plurality of longitudinally extending fingers separated by gaps or spaces.

16. The surgical device defined in claim 9 wherein said distal end portion of said sheath or sleeve has a distal-most edge and is provided with at least one aperture in a sidewall, said aperture being spaced from said edge.

* * * * *